United States Patent [19]

Ellis et al.

[11] Patent Number: 4,686,101

[45] Date of Patent: Aug. 11, 1987

[54] VACCINE AGAINST VARICELLA-ZOSTER VIRUS

[75] Inventors: Ronald W. Ellis, Overbrook Hills; Robert S. Lowe, Harleysville; Paul M. Keller, Lansdale, all of Pa.; Andrew J. Davison, Glasgow, Scotland

[73] Assignee: Merck & Co., Inc., Rahway, N.J.

[21] Appl. No.: 762,001

[22] Filed: Aug. 2, 1985

[51] Int. Cl.⁴ .................... A61K 39/00; C07K 13/00
[52] U.S. Cl. .................................... 424/88; 530/350
[58] Field of Search .......................... 435/84; 424/88; 530/350

[56] References Cited

U.S. PATENT DOCUMENTS 4,452,734  6/1984  Larson et al. .................... 435/84

OTHER PUBLICATIONS

J. Gen. Virol. (1985) 66, 2237-2242, Davison, et al.
J. of Virology, Mar., (1985) 761-770, vol. 53, No. 3, Montalvo, et al.
J. Gen. Virol. (1985) 66, 207-220, Davison, et al.
Virology 106, 133-140 (1980) Shemer, et al.
J. Gen. Virol. (1983) 64, 1181-1186, Lopetegui, et al.
Virology 129, 357-368 (1983).
J. of Virology (1984) 293-297 52.
J. of Virology (1984) 55-62, vol. 52.
Virology 132, 138-146 (1984).
J. of Virology (1984) 953-959, vol. 52.
Virology 143, 252-259 (1985).

*Primary Examiner*—Delbert R. Phillips
*Attorney, Agent, or Firm*—Donald J. Perrella; Hesna J. Pfeiffer

[57] ABSTRACT

A gene of varicella-zoster virus (VZV) which encodes immunogenic outer surface viral proteins has been identified by DNA sequence analysis. This gene can hybrid select messenger RNA which encodes and expresses a protein which reacts with human canvalescent zoster sera and with polyclonal monospecific antisera which neutralize viral infectivity. These proteins are useful for the preparation of a vaccine for VZV.

2 Claims, No Drawings

VACCINE AGAINST VARICELLA-ZOSTER VIRUS

BACKGROUND OF THE INVENTION

Chickenpox is caused by varicella-zoster virus (VZV), a member of the herpesvirus group. The disease occurs in persons with no prior VZV immunity. VZV-specific antibodies can be demonstrated shortly after onset of disease, decline during convalescence, but remain detectable for many years and correlate with immunity to the disease. Chickenpox is highly contagious; over 90% of the population becomes exposed to VZV before they are 20 years old. In most, if not all cases, VZV apparently becomes latent in dorsal root ganglion cells. From this latent state, VZV can reactivate and cause zoster even in the presence of specific antibodies, probably as a result of weakened cellular immunity. The disease is highly morbid to the immunosuppressed and to those beyond the second decade.

VZV has five major glycoproteins on its surface: gp115 (115,000 dalton glycoprotein), gp105, gp92, gp83, gp55. These glycoproteins apparently are the products of three genes: gA (gp105), gB (gp115, in the non-reduced state, composed of the reduced species gp62 and gp57), and gC (gp92, gp83, gp55). Monoclonal antibodies to gA and gB display complement-independent neutralization, and monoclonal antibodies to gC display complement-dependent neutralization.

OBJECTS OF THE INVENTION

It is an object of the present invention to provide antigens which will prevent diseases associated with VZV infections. Another object is to provide antigens which can be used diagnostically to measure VZV antibody titers. Another object is to provide methods for the preparation of these antigens. Another object is to provide methods for using the antigens to raise antibodies, both in vivo and in vitro, to VZV. Another object is to describe the full sequence of protein antigens which will include peptide antigens which may be synthesized by other means or expressed in expression vectors. These and other objects of the present invention will be apparent from the following description.

SUMMARY OF THE INVENTION

The DNA sequence of the VZV gB gene has been identified. A fragment of this sequence has been used to hybrid-select mRNA from VZV-infected cells. In vitro translational products from this mRNA have been immunoprecipitated by guinea pig antibodies raised to gB purified by monoclonal antibody affinity chromatography. Such proteins are useful for the preparation of a vaccine to VZV.

DETAILED DESCRIPTION OF THE INVENTION

The present invention is directed to the identification of the VZV DNA segment which encodes the protective immunogenic gB glycoproteins. More specifically, it is directed to a 2.6 Kilobase pair (Kbp) DNA fragment whose respective nucleotide sequence and derived amino acid sequences have been located within the known sequence of the entire VZV genome.

The present invention also is directed to vectors containing all or part of this 2.6 Kbp DNA fragment. The invention also is directed to host cells which contain these vectors and which cells are capable of expressing all or part of the peptides encoded by the 2.6 Kbp fragment. In accordance with known techniques, it will be obvious to those skilled in the art that parts of the foregoing peptides could be chemically synthesized or modified and retain their immunogenicity. Therefore, the present invention also is directed toward chemical synthesis of domains of these proteins, especially domains including and surrounding hydrophilic regions and threonine or serine and asparagine-X-serine or asparagine-X-threonine residues wherein X is any amino acid residue, since these domains are likely to reside on the outer surface of the virus.

The DNA segment which encodes RNA translatable to gB polypeptides is identified precisely as follows:

Several viral glycoproteins, gp115, gp62 and gp57 (also referred to as gp1 and gp3 or "disulfide-linked dimer") are crossreactive with monoclonal antibodies and have been proposed to be the products of the gB glycoprotein gene. In order to map this gene on the VZV genome, plasmids from a VZV genomic DNA library have been used to hybrid-select RNA from VZV-infected cells. In vitro translational products are immunoprecipitated by guinea pig antibodies raised to gB purified by monoclonal antibody affinity chromatography. These antibodies are capable of neutralizing viral infectivity. By this analysis, it is found that a 100 Kilodalton (KD) polypeptide can be immunoprecipitated from mRNA selected by the HindIII-D fragment. DNA sequence analysis of this region of the VZV genome reveals a 2.6 kbp open reading frame (ORF) which could encode a 100 KD protein with a glycoprotein-like structure (hydrophobic leader, hydrophobic anchor, 9 N-glycosylation recognition sites). This ORF DNA is cloned from the HindIII-D fragment and shown capable of hybrid-selecting mRNA with a 100 KD translational product. Furthermore, the immunoprecipitability of the 100 KD species can be blocked specifically by immune-affinity purified gB. In addition, VZV gB has been purified by immune-affinity chromatography. When injected to guinea pigs, this protein is capable of eliciting the formation of antibodies which neutralize VZV infecivity in vitro. Partial amino acid sequence analysis of the purified VZV gB reveals identity to the amino acid sequence imputed from the DNA sequence of the 2.6 kbp ORF. We conclude that this ORF in the HindIII-D fragment is the glycoprotein gB gene and specifies a gene product carrying neutralization epitopes.

In accordance with known techniques, it will be obvious to those skilled in the art that all or part of the above-mentioned DNA fragment can be placed into an expression vector system in order to produce all or part of the protective immunogenic polypeptide. Such an expression vector system often consists of a plasmid which is inserted into a prokaryotic or eukaryotic cell in order to direct expression of a foreign polypeptide. Such a plasmid usually contains sequences for selection of host cells containing the plasmid, for amplification of plasmid copy number within the host cell, for initiation of transcription of the foreign polypeptide, for termination of transcription of the foreign polypeptide, in addition to the coding sequence per se which specifies the foreign polypeptide. Therefore, the present invention also is directed to host cells and vectors containing all or part of the 2.6 Kbp DNA fragment.

Examples of suitable hosts for expression of VZV proteins include prokaryotic organisms, such as E coli and B. subtilis, and eukaryotic organisms such as S.

*cerevisiae* and continuous mammalian cell lines including but not limited to Chinese Hamster Ovary cells and Vero cells.

These proteins are useful individually or in combination when placed in a physiologically acceptable carrier, e.g., saline or phosphate buffered saline, to protect against VZV disease when administered to a member of a susceptible mammalian species, in amount of approximately 5 to 150 mcg per dose, preferably from approximately 10 to 50 mcg per dose. One or more doses may be administered to produce effective protection against VZV disease. The protein may be administered by injection, e.g., subcutaneously or intramuscularly. It is also to be understood that these proteins can be directly expressed in humans by means of appropriate viral expression vectors such as adeno, vaccinia, or herpes simplex.

The following examples illustrate the present invention without, however, limiting the same thereto. The disclosure of each reference mentioned in the following examples is hereby incorporated by reference.

EXAMPLE I

DNA fragment which can select RNA encoding the precursor protein to gB glycoproteins.

Cytoplasmic RNAs were prepared from VZV-infected MRC-5 cells as described (J. M. Chirgwin et al., Biochemistry 18: 5294 (1979)). The RNAs encoded by the different VZV HindIII fragments were selected by hybridization to cloned VZV HindIII DNA fragments (J. R. Ecker & R. W. Hyman, Proc. Natl. Acad. Sci. U.S.A. 79: 156 (1982)) bound to nitrocellulose (J. A. Cooper et al., J. Virology 37: 284 (1981)). These RNAs were translated in a rabbit reticulocyte lysate. The polypeptide products were immunoprecipitated by polyclonal monospecific guinea pig antibodies raised to gB purified by monoclonal antibody affinity chromatography. (This purification is described below in Example V). By this analysis, it was found that a 100 KD in vitro translational product from mRNA selected by the VZV HindIII-D fragment could be immunoprecipitated by the anti-gB antibodies which neutralize viral infectivity. (The neutralization data are described below in Example IV).

EXAMPLE II

DNA fragment of HindIII-D DNA containing a large ORF

Sequence analysis of the HindIII-D fragment from the VZV genome revealed an ORF which could encode a 100 KD protein with a glycoprotein-like structure (hydrophobic leader, hydrophobic anchor, 9 N-glycosylation recognition sites). A segment of this ORF DNA was cloned from the HindIII-D fragment and shown capable of hybrid selecting mRNA with a 100 KD translational product which was immunoprecipitable both by monospecific guinea pig sera and convalescent zoster sera. Furthermore, the immunoprecipitability by both sera of the 100 KD species could be blocked specifically by immune-affinity purified gB but not by another major VZV glycoprotein. Therefore, this segment of HindIII-D DNA was identified as the gB gene.

EXAMPLE III

Determination of nucleotide sequences of the 2.6 kbp segment of VZV DNA.

The complete nucleotide sequence of the VZV HindIII-D DNA segment contains several large open reading frames. One of these open reading frames is 2.6 kbp in length, encodes a 100 KD protein, and contains the segment described in Example II which encodes VZV gB antigens. The nucleotide sequence for the complete 2.6 kbp segment which encodes the gB glycoprotein is given below:

|     |     |     |     |     |     |     |     | ATG | TTT | GTT | ACG | GCG | GTT |
| --- | --- | --- | --- | --- | --- | --- | --- | --- | --- | --- | --- | --- | --- |
| GTG | TCG | GTC | TCT | CCA | AGC | TCG | TTT | TAT | GAG | AGT | TTA | CAA | GTA |
| GAG | CCC | ACA | CAA | TCA | GAA | GAT | ATA | ACC | CGG | TCT | GCT | CAT | CTG |
| GGC | GAT | GGT | GAT | GAA | ATC | AGA | GAA | GCT | ATA | CAC | AAG | TCC | CAG |
| GAC | GCC | GAA | ACA | AAA | CCC | ACG | TTT | TAC | GTC | TGC | CCA | CCG | CCA |
| ACA | GGC | TCC | ACA | ATC | GTA | CGA | TTA | GAA | CCA | ACT | CGG | ACA | TGT |
| CCG | GAT | TAT | CAC | CTT | GGT | AAA | TTT | ACA | GAG | GGT | ATT | GCT |
| GTT | GTT | TAT | AAA | GAA | AAC | ATT | GCA | GCG | TAC | AAG | TTT | AAG | GCG |
| ACG | GTA | TAT | TAC | AAA | GAT | GTT | ATC | GTT | AGC | ACG | GCG | TGG | GCC |
| GGA | AGT | TCT | TAT | ACG | CAA | ATT | ACT | AAT | AGA | TAT | GCG | GAT | AGG |
| GTA | CCA | ATT | CCC | GTT | TCA | GAG | ATC | ACG | GAC | ACC | ATT | GAT | AAG |
| TTT | GGC | AAG | TGT | TCT | TCT | AAA | GCA | ACG | TAC | GTA | CGA | AAT | AAC |
| CAC | AAA | GTT | GAA | GCC | TTT | AAT | GAG | GAT | AAA | AAT | CCA | CAG | GAT |
| ATG | CCT | CTA | ATC | GCA | TCA | AAA | TAT | AAT | TCT | GTG | GGA | TCC | AAA |
| GCA | TGG | CAT | ACT | ACC | AAT | GAC | ACG | TAC | ATG | GTT | GCC | GGA | ACC |
| CCC | GGA | ACA | TAT | AGG | ACG | GGC | ACG | TCG | GTG | AAT | TGC | ATC | ATT |
| GAG | GAA | GTT | GAA | GCC | AGA | TCA | ATA | TTC | CCT | TAT | GAT | AGT | TTT |
| GGA | CTT | TCC | ACG | GGA | GAT | ATA | ATA | TAC | ATG | TCC | CCG | TTT | TTT |
| GGC | CTA | CGG | GAT | GGT | GCA | TAC | AGA | GAA | CAT | TCC | AAT | TAT | GCA |
| ATG | GAT | CGT | TTT | CAC | CAG | TTT | GAG | GGT | TAT | AGA | CAA | AGG | GAT |
| CTT | GAC | ACT | AGA | GCA | TTA | CTG | GAA | CCT | GCA | GCG | CGG | AAC | TTT |
| TTA | GTC | ACG | CCT | CAT | TTA | ACG | GGT | TGG | AAC | TGG | AAG | CCA |
| AAA | CGA | ACG | GAA | GTT | TGT | TCG | CTT | GTC | AAG | TGG | CGT | GAG | GTT |
| GAA | GAC | GTA | GTT | CGC | GAT | GAG | TAT | GCA | CAC | AAT | TTT | CGC | TTT |
| ACA | ATG | AAA | ACA | CTT | TCT | ACC | ACG | TTT | ATA | AGT | GAA | ACA | AAC |
| GAG | TTT | AAT | CTT | AAC | CAA | ATC | CAT | CTC | AGT | CAA | TGT | GTA | AAG |
| GAG | GAA | GCC | CGG | GCT | ATT | ATT | AAC | CGG | ATC | TAT | ACA | ACC | AGA |
| TAC | AAC | TCA | TCT | CAT | GTT | AGA | ACC | GGG | GAT | ATC | CAG | ACC | TAC |
| CTT | GCC | AGA | GGG | GGG | TTT | GTT | GTG | GTG | TTT | CAA | CCC | CTG | CTG |
| AGC | AAT | TCC | CTC | GCC | CGT | CTC | TAT | CTC | CAA | GAA | TTG | GTC | CGT |
| GAA | AAC | ACT | AAT | CAT | TCA | CCA | CAA | AAA | CAC | CCG | ACT | CGA | AAT |
| ACC | AGA | TCC | CGA | CGA | AGC | GTG | CCA | GTT | GAG | TTG | CGT | GCC | AAT |
| AGA | ACA | ATA | ACA | ACC | ACC | TCA | TCG | GTG | GAA | TTT | GCT | ATG | CTC |
| CAG | TTT | ACA | TAT | GAC | CAC | ATT | CAA | GAG | CAT | GTT | AAT | GAA | ATG |
| TTG | GCA | CGT | ATC | TCC | TCG | TCG | TGG | TGC | CAG | CTA | CAA | AAT | CGC |

-continued

| | | | | | | | | | | | | | |
|---|---|---|---|---|---|---|---|---|---|---|---|---|---|
| GAA | CGC | GCC | CTT | TGG | AGC | GGA | CTA | TTT | CCA | ATT | AAC | CCA | AGT |
| GCT | TTA | GCG | AGC | ACC | ATT | TTG | GAT | CAA | CGT | GTT | AAA | GCT | CGT |
| ATT | CTC | GGC | GAC | GTT | ATC | TCC | GTT | TCT | AAT | TGT | CCA | GAA | CTG |
| GGA | TCA | GAT | ACA | CGC | ATT | ATA | CTT | CAA | AAC | TCT | ATG | AGG | GTA |
| TCT | GGT | AGT | ACT | ACG | CGT | TGT | TAT | AGC | CGT | CCT | TTA | ATT | TCA |
| ATA | GTT | AGT | TTA | AAT | GGG | TCC | GGG | ACG | GTG | GAG | GGC | CAG | CTT |
| GGA | ACA | GAT | AAC | GAG | TTA | ATT | ATG | TCC | AGA | GAT | CTG | TTA | GAA |
| CCA | TGC | GTG | GCT | AAT | CAC | AAG | CGA | TAT | TTT | CTA | TTT | GGG | CAT |
| CAC | TAC | GTA | TAT | TAT | GAG | GAT | TAT | CGT | TAC | GTC | CGT | GAA | ATC |
| GCA | GTC | CAT | GAT | GTG | GGA | ATG | ATT | AGC | ACT | TAC | GTA | GAT | TTA |
| AAC | TTA | ACA | CTT | CTT | AAA | GAT | AGA | GAG | TTT | ATG | CCG | CTG | CAA |
| GTA | TAT | ACA | AGA | GAC | GAG | CTG | CGG | GAT | ACA | GGA | TTA | CTA | GAC |
| TAC | AGT | GAA | ATT | CAA | CGC | CGA | AAT | C (5) 3M KSCN; (6) 0.1M NaHBO4, pH 8.2; then stored in 0.1M NaHBO4, pH 8.2 at 4° C. prior to use.

VZV glycoproteins were purified from MRC-5 human diploid fibroblasts which were infected with VZV to the extent of 80% cytopathic effect. Cells in 750 cm² roller bottles were washed twice with 0.15M NaCl, 0.01M Na2HPO4, pH 7.2 and drained well. Ten ml of 50 mM Tris, pH 7.5, 2% Triton X-100, 4 mM phenylmethylsulfonylfluoride (PMSF) were incubated 15° to the bottle while rolling. The same 10 ml then was used to successively extract 9 more roller bottles. A fresh 10 ml aliquot of buffer was used to successively rinse the 10 roller bottles and pooled with the first aliquot, such that 20 ml of extract represent material from 10 roller bottles. Extracts were stored at −70° C. until use.

Extracts were thawed and dialyzed overnight at 4° C. against 0.15M NaCl, 0.01M Na2HPO4, 0.05% Triton X-100, pH 7.2, then clarified by centrifuging at 1500 rpm for 15 minutes at 4° C. 20 ml of extract were added to 1 g of monoclonal antibody-coupled resin and incubated overnight at 4° C. with shaking. The slurry was centrifuged for 15 minutes at 1500 rpm at 4° C. and washed three times with 0.1M NaHBO4, pH 8.2. The glycoprotein was eluted by incubation at 23° C. with 10 ml 3M KSCN. The eluate was immediately dialyzed against 0.15M NaCl, 0.01M Na2HPO4, 0.05% Triton X-100, pH 7.2 overnight at 4° C. and concentrated to approximately 1 mg/ml.

Of the immune-affinity purified gB, approximately 500 μg was loaded into the sample loop of a LCC (Liquid Chromatography Controller) 500 FPLC (Fast Protein Liquid Chromatography) (Pharmacia). The sample then was injected onto a Mono Q anion exchange column (Pharmacia) followed by a 5 ml wash with 20 mM Tris, pH 7.7, 20 mM CHAPS (Sigma). A gradient of 0-1M NaCl in 20 mM Tris, pH 7.5, 20 mM CHAPS was run over the column, and individual fractions were collected. At approximately 0.3M NaCl, there was eluted a single major homogeneous peak which was concentrated in a Centricon concentrator (Amicon) to a volume of 50 μl in 10 mM Tris, pH 7.5, 10 mM NaCl, 0.05% Triton X-100. This peak was verified as VZV gB by the following criteria. In silver strains of sodium dodecyl sulfate-polyacrylamide gel electrophoresis (SDS-PAGE) run under reducing conditions, the sample was resolved as two proteins of molecular weights 62,000 and 53,000 daltons, as described in Keller et al., ibid., i.e., gp62, gp57; Okuno et al., Virology 129: 357 (1983), i.e., gp5; Grose et al., Virology 132: 138 (1984), i.e., gp66, "disulfide-linked dimer"; Inghani et al., J. Virology, 52: 55 (1984), i.e., 64K-65K. In silver strains of SDS PAGE run under non-reducing conditions, the sample was resolved as a single protein of molecular weight 115,000, as described in Grose et al. ibid., i.e., gp 140, Vafai et al., J. Virology 52: 953 (1984), i.e., gp 130.

EXAMPLE V

Purified VZV gB polypeptide induces antibodies which neutralize VZV infectivity in vitro Guinea pigs were inoculated intramuscularly with 20 micrograms in complete Freund's adjuvant of VZV gB (purified by immune-affinity chromatography as described above in Example IV), followed one month later by two inoculations each of ten micrograms of VZV gB in incomplete Freund's adjuvant spaced two weeks apart. Sera were obtained from the guinea pigs after these three inoculations. Each of the guinea pig sera were utilized in an in vitro VZV neutralization assay as described (Keller et al., ibid.). By this assay the post-immunization but not the pre-immunization sera elicited VZV neutralizing antibodies.

EXAMPLE VI

Amino acid analysis of purified VZV gB polypeptide

300 μg of VZV gB (purified as described in Example IV) was subjected to amino terminal sequence analysis using an applied Biosystems Gas-Phase Sequenator [Hewick et al., J. Biol. Chem. 256: 7790 (1981)]. The PTH (phenylthiohydantoin) amino acids produced at each step were separated and quantitated by high performance liquid chromatography Speiss et al., Proc. Natl. Acad. Sci., U.S.A. 70: 2974 (1979).

The sequence analysis demonstrated that gB contains two distinct amino termini consistent with the analysis described above in Example IV. Each cycle of the sequenator revealed 0, 1 or 2 identifiable amino acids. In all, 11 amino acids in gB were identified. Six of these could be aligned within the sequence of amino acids 9–20 imputed from the DNA sequence in Example III above. Five of these could be aligned within the sequence of amino acids 432–443 imputed from the DNA sequence in Example III above. Since the imputed amino acid sequence contains 868 amino acids, these sequence data of the purified VZV gB are consistent with a cleavage event that partitions the protein to two polypeptides, each approximately containing 430 amino acids. This is consistant with the closely familar molecular weights of the two reduced species of VZV gB, i.e., gp62 and gp57.

FIG. 1
Amine acid sequence analysis of purified VZV gB

|   |     |     |     |     |     |     |     |     |     |     |     |     |
|---|-----|-----|-----|-----|-----|-----|-----|-----|-----|-----|-----|-----|
| 1 | val | ser | pro | ser | ser | phe | tyr | glu | ser | leu | gln | val |
| 2 | —   | —   | pro | —   | —   | phe | tyr | —   | —   | leu | gln | val |
|   | —   | —   | pro | val | —   | leu | —   | ala | —   | —   | —   | ile |
| 3 | ser | val | pro | val | glu | leu | arg | ala | asn | arg | thr | ile |

1 = imputed amino acids 9–20 from Example III
2 = amino acid sequence of purified VZV gB wherein a dash (—) means that no amino acid was resolved at that position
3 = imputed amino acids 432–443 from Example III

What is claimed is:
1. A purified polypeptide having the amino acid sequence:

Met Phe Val Thr Ala Val
Val Ser Val Ser Pro Ser Ser Phe Tyr Glu Ser Leu Gln Val
Glu Pro Thr Gln Ser Glu Asp Ile Thr Arg Ser Ala His Leu
Gly Asp Gly Asp Glu Ile Arg Glu Ala Ile His Lys Ser Gln
Asp Ala Glu Thr Lys Pro Thr Phe Tyr Val Cys Pro Pro Pro
Thr Gly Ser Thr Ile Val Arg Leu Glu Pro Thr Arg Thr Cys
Pro Asp Tyr His Leu Gly Lys Asn Phe Thr Glu Gly Ile Ala
Val Val Tyr Lys Glu Asn Ile Ala Ala Tyr Lys Phe Lys Ala

-continued

Thr Val Tyr Tyr Lys Asp Val Ile Val Ser Thr Ala Trp Ala
Gly Ser Ser Tyr Thr Gln Ile Thr Asn Arg Tyr Ala Asp Arg
Val Pro Ile Pro Val Ser Glu Ile Thr Asp Thr Ile Asp Lys
Phe Gly Lys Cys Ser Ser Lys Ala Thr Tyr Val Arg Asn Asn
His Lys Val Glu Ala Phe Asn Glu Asp Lys Asn Pro Gln Asp
Met Pro Leu Ile Ala Ser Lys Tyr Asn Ser Val Gly Ser Lys
Ala Trp His Thr Thr Asn Asp Thr Tyr Met Val Ala Gly Thr
Pro Gly Thr Tyr Arg Thr Gly Thr Ser Val Asn Cys Ile Ile
Glu Glu Val Glu Ala Arg Ser Ile Phe Pro Tyr Asp Ser Phe
Gly Leu Ser Thr Gly Asp Ile Ile Tyr Met Ser Pro Phe Phe
Gly Leu Arg Asp Gly Ala Tyr Arg Glu His Ser Asn Tyr Ala
Met Asp Arg Phe His Gln Phe Glu Gly Tyr Arg Gln Arg Asp
Leu Asp Thr Arg Ala Leu Leu Glu Pro Ala Ala Arg Asn Phe
Leu Val Thr Pro His Leu Thr Val Gly Trp Asn Trp Lys Pro
Lys Arg Thr Glu Val Cys Ser Leu Val Lys Trp Arg Glu Val
Glu Asp Val Val Arg Asp Glu Tyr Ala His Asn Phe Arg Phe
Thr Met Lys Thr Leu Ser Thr Thr Phe Ile Ser Glu Thr Asn
Glu Phe Asn Leu Asn Gln Ile His Leu Ser Gln Cys Val Lys
Glu Glu Ala Arg Ala Ile Ile Asn Arg Ile Tyr Thr Thr Arg
Tyr Asn Ser Ser His Val Arg Thr Gly Asp Ile Gln Thr Tyr
Leu Ala Arg Gly Gly Phe Val Val Val Phe Gln Pro Leu Leu
Ser Asn Ser Leu Ala Arg Leu Tyr Leu Gln Glu Leu Val Arg
Glu Asn Thr Asn His Ser Pro Gln Lys His Pro Thr Arg Asn
Thr Arg Ser Arg Arg Ser Val Pro Val Glu Leu Arg Ala Asn
Arg Thr Ile Thr Thr Thr Ser Ser Val Glu Phe Ala Met Leu
Gln Phe Thr Tyr Asp His Ile Gln Glu His Val Asn Glu Met
Leu Ala Arg Ile Ser Ser Ser Trp Cys Gln Leu Gln Asn Arg
Glu Arg Ala Leu Trp Ser Gly Leu Phe Pro Ile Asn Pro Ser
Ala Leu Ala Ser Thr Ile Leu Asp Gln Arg Val Lys Ala Arg
Ile Leu Gly Asp Val Ile Ser Val Ser Asn Cys Pro Glu Leu

-continued

Gly Ser Asp Thr Arg Ile Ile Leu Gln Asn Ser Met Arg Val
Ser Gly Ser Thr Thr Arg Cys Tyr Ser Arg Pro Leu Ile Ser
Ile Val Ser Leu Asn Gly Ser Gly Thr Val Glu Gly Gln Leu
Gly Thr Asp Asn Glu Leu Ile Met Ser Arg Asp Leu Leu Glu
Pro Cys Val Ala Asn His Lys Arg Tyr Phe Leu Phe Gly His
His Tyr Val Tyr Tyr Glu Asp Tyr Arg Tyr Val Arg Glu Ile
Ala Val His Asp Val Gly Met Ile Ser Thy Tyr Val Asp Leu
Asn Leu Thr Leu Leu Lys Asp Arg Glu Phe Met Pro Leu Gln
Val Tyr Thr Arg Asp Glu Leu Arg Asp Thr Gly leu Leu Asp
Tyr Ser Glu Ile Gln Arg Arg Asn Gln Met His Ser Leu Arg
Phe Tyr Asp Ile Asp Lys Val Val Gln Tyr Asp Ser Gly Thr
Ala Ile Met Gln Gly Met Ala Gln Phe Phe Gln Gly Leu Gly
Thr Ala Gly Gln Ala Val Gly His Val Val Leu Gly Ala Thr
Gly Ala Leu Leu Ser Thr Val His Gly Phe Thr Thr Phe Leu
Ser Asn Pro Phe Gly Ala Leu Ala Val Gly Leu Leu Val Leu
Ala Gly Leu Val Ala Ala Phe Phe Ala Tyr Arg Tyr Val Leu
Lys Leu Lys Thr Ser Pro Met Lys Ala Leu Tyr Pro Leu Thr
Thr Lys Gly Leu Lys Gln Leu Pro Glu Gly Met Asp Pro Phe
Ala Glu Lys Pro Asn Ala Thr Asp Thr Pro Ile Glu Glu Ile
Gly Asp Ser Gln Asn Thr Glu Pro Ser Val Asn Ser Gly Phe
Asp Pro Asp Lys Phe Arg Glu Ala Gln Glu Met Ile Lys Tyr
Met Thr Leu Val Ser Ala Ala Glu Arg Gln Glu Ser Lys Ala
Arg Lys Lys Asn Lys Thr Ser Ala Leu Leu Thr Ser Arg Leu
Thr Gly Leu Ala Leu Arg Asn Arg Arg Gly Tyr Ser Arg Val
Arg Thr Glu Asn Val Thr Gly Val.

2. A composition useful for immunizing against VZV comprising an immunologically effective amount of the polypeptide of claim 1 or an immunologic subunit thereof in a physiologically acceptable carrier.

* * * * *